United States Patent

Desinger et al.

(10) Patent No.: US 8,216,219 B2
(45) Date of Patent: Jul. 10, 2012

(54) DEVICE FOR ELECTROSURGICALLY DESTROYING BODY TISSUE

(75) Inventors: Kai Desinger, Berlin (DE); Thomas Stein, Berlin (DE); Andre Roggan, Berlin (DE); Thomas Prezewowsky, Teltow (DE)

(73) Assignee: Celon AG, Berlin (DE)

( * ) Notice: Subject to any disclaimer, the term of this patent is extended or adjusted under 35 U.S.C. 154(b) by 2269 days.

(21) Appl. No.: 10/515,945

(22) PCT Filed: May 23, 2003

(86) PCT No.: PCT/EP03/05439
§ 371 (c)(1),
(2), (4) Date: Jul. 22, 2005

(87) PCT Pub. No.: WO03/099372
PCT Pub. Date: Dec. 4, 2003

(65) Prior Publication Data
US 2006/0015095 A1    Jan. 19, 2006

(30) Foreign Application Priority Data

May 27, 2002  (DE) ................................. 102 24 154
Apr. 10, 2003  (DE) ................................. 103 17 243

(51) Int. Cl.
*A61B 18/10* (2006.01)

(52) U.S. Cl. ............................. 606/34; 606/41; 607/101
(58) Field of Classification Search ............. 606/27–34, 606/41, 42; 607/96–101
See application file for complete search history.

(56) References Cited

U.S. PATENT DOCUMENTS

| 5,383,917 | A  | * | 1/1995 | Desai et al. ................... 607/102 |
| 5,630,426 | A  |   | 5/1997 | Eggers |
| 6,092,528 | A  | * | 7/2000 | Edwards ........................ 128/898 |
| 6,261,286 | B1 | * | 7/2001 | Goble et al. ..................... 606/34 |
| 6,293,942 | B1 | * | 9/2001 | Goble et al. ..................... 606/38 |
| 6,301,496 | B1 | * | 10/2001 | Reisfeld ........................ 600/407 |
| 6,306,134 | B1 | * | 10/2001 | Goble et al. ..................... 606/42 |
| 2002/0120261 | A1 | * | 8/2002 | Morris et al. ................... 606/41 |

* cited by examiner

*Primary Examiner* — Michael Peffley
(74) *Attorney, Agent, or Firm* — Oliff & Berridge, PLC

(57) ABSTRACT

An electrode array is used for the thermal schlerosing of body tissue. The electrode array has at least three active electrodes that, during use, are placed in electrical-conducting connection with body tissue. A high frequency generator is electrically connected for selective application of current to the active electrodes for producing a high frequency voltage. A measuring device measures impedance of the tissue between the active electrodes. In addition, a selector device selects a sub-array including at least two active electrodes from the electrode array, the selecting being effected on the basis of the measured impedance. Further, a control device is configured such that a high frequency voltage is respectively applied between the active electrodes of the selected sub-array in such a way that a high frequency current flows between the selected active electrodes through the body tissue.

23 Claims, 4 Drawing Sheets

DEVICE FOR ELECTROSURGICALLY DESTROYING BODY TISSUE

This application claims priority to PCT/EP03/05439, filed May 23, 2003 and to DE 102 24 154.6, filed May 27, 2002 and to DE 103 17 243.2, filed Apr. 10, 2003.

FIELD OF THE INVENTION

The present invention concerns an application apparatus for applying a high frequency current for thermal sclerosis of body tissue. The application apparatus includes an electrode array with at least three active electrodes which can be introduced into body tissue. The application apparatus further includes a high frequency generator for producing a high frequency voltage, which generator is to be switchably connected to one or more of the electrodes, and a measuring device for measuring the impedance of the body tissue between all or selected active electrodes.

BACKGROUND OF THE INVENTION

Electrosurgical and in particular electrothermal sclerosing of pathologically altered tissue, hereinafter referred to for brevity as tissue, is a method which is known in medicine. That method is of particular interest for the therapy of organ tumors, in particular liver tumors. For the sclerosing procedure, one or more electrodes are placed in the tissue to be sclerosed, that is to say the tumor tissue, or in the immediate proximity thereof, and an alternating current is caused to flow between the electrodes or an electrode and a neutral electrode fixed externally to the body. If the current flows between the electrode and the neutral electrode (possibly also between a plurality of electrodes and one or more neutral electrodes), that is referred to as a monopolar electrode arrangement. If in contrast the current flows between the electrodes themselves disposed in the tissue (in that case there must be at least two electrodes in the tissue), that is to referred to as a bipolar arrangement. An arrangement is referred to as a multipolar arrangement when more than two electrodes between which alternating current flows are present in the tissue.

The electrodes intended for placement in the tissue are generally in the form of electrode needles. They have an electrically conducting cylindrical shaft which, with the exception of one or more distal regions, the so-called active regions of the electrode or, for brevity, active electrodes, is electrically insulated relative to the ambient tissue. In contrast the active electrodes are electrically conductively connected to the body tissue. The active electrodes are optionally also equipped with integrated thermosensors. In especial embodiments further active electrodes can be mechanically extended at the distal end of the shaft in order to enlarge the volume of tissue to which therapy can be applied.

A flow of current is induced between the active electrodes and the neutral electrode or electrodes by means of a high frequency generator, in the monopolar arrangement. In the alternative bipolar arrangement, it is possible to eliminate the neutral electrodes. In that case the circuit is closed by way of a further active electrode, in which respect the required active electrodes can be arranged in a coaxial configuration in mutually insulated relationship on the electrode needle or on two separate electrode needles.

The ohmic resistance of the tissue, which is a part of the complex tissue impedance, causes the alternating current applied by way of the electrodes to be converted into joulean heat. At temperatures of between 50 and 100° C., massive denaturisation of the body-specific proteins (coagulation) occurs and consequently the tissue area in question is caused to die off. By virtue of the high current density at the active electrodes heating takes place predominantly in the region of those electrodes so that local thermal tumor destruction is possible.

An apparatus for and a method of electrothermal sclerosing of pathological tissue is disclosed by way of example in U.S. Pat. No. 5,630,426.

What is crucial for effective and in particular reliable therapy is the production of a thermal destruction zone which is optimally adapted to the extent of the pathological tissue, that is to say the tumor tissue.

SUMMARY OF THE INVENTION

The object of the present invention is to provide an apparatus for electrothermal sclerosing of tissues, which permits reliable destruction of pathological tissue.

That object is attained by an apparatus for applying a high frequency current of the kind set forth in the opening part of this specification, which has a selector device which is connected to the measuring device and which is adapted to select a sub-array including at least two active electrodes from the electrode array on the basis of the measured impedance. The apparatus for applying a high frequency current also has a control device which is connected to the selector device and which is adapted to apply the high frequency voltage to the active electrodes of the selected sub-array in such a way that a high frequency current flows between them through the body tissue.

In a preferred arrangement the application apparatus is of such a configuration that the high frequency generator, the measuring device, the selector device and the control device are combined in one or more housings to form an application generator which has plug connections for the electrodes and for the feed lines thereof. The electrodes can thus be connected selectively to the application generator.

The application generator preferably includes a connection detection unit which is connected to the plug connections and adapted to automatically detect that an electrode is connected to a plug connection. The connection detection unit is preferably connected to the control unit.

The control unit is in turn preferably of such a configuration that all connected electrodes are incorporated into an electrotherapy so that in the course of a predetermined time a high frequency voltage is applied at least once to each connected electrode by means of the selector device.

In an alternative configuration switches can be provided on the application generator, with which given electrodes can be selectively switched off in such a way that no high frequency voltage is applied in the above-indicated manner to a switched-off electrode.

The further appendant claims recite further advantageous configurations of the invention.

The invention is based on the realisation that the electrode arrangement in the tumor plays a crucial part in terms of the production of a destruction zone which is optimally adapted to the tumor tissue. In clinical practice it is in the meantime usual when dealing with relatively large tissue areas to be destroyed to position a plurality of electrode needles in the tissue in order to achieve an increase in efficiency by means of superposition of the thermal destruction zones produced by the individual electrodes. In addition, in some uses, a uniform thermal destruction zone is to be achieved by multi-channel temperature measurement. In practice however that has proven to be inadequate because that only involves point measurements and it is not possible to take account of the tissue properties at some distance from the measurement locations. That repeatedly involves under-therapy, that is to say the temperature required for total destruction of the tumor tissue is not reached in tissue areas which are to be treated. Consequently the patients suffer from a relapse and have to be subjected to therapy again.

Tissue impedance depends greatly on the advance of the thermal tissue destruction. With increasing sclerosing of the tissue in particular its ohmic resistance and therewith also impedance rises. The underlying concept of the invention is the fact that, in contrast to temperature, tissue impedance represents an item of volume information which integrally describes the tissue properties between the two measurement locations necessary for impedance measurement. In accordance with the invention therefore the change in impedance characteristic in combination with a multipolar application arrangement is to be utilised for optimum therapy control. It is surprisingly found that, in a situation involving multiple application, that is to say high frequency currents are caused to flow between a plurality of active electrode pairs, tissue impedance between the individual active electrodes does not exhibit a uniform behaviour. Rather, the tissue between individual active electrode pairs can already have made the transition into the drying-out condition, in which case it is of very high impedance, while the tissue between other active electrode pairs has not yet reached that condition and accordingly exhibits very low impedance. That correlates with the clinical recognition that, even with point temperature measurement, it is not possible to guarantee reliable volume destruction. Causes of that non-homogenous drying-out of the body tissue are for example blood vessels which are not uniformly distributed and which exert a locally delimited cooling effect and thus counteract the therapy effect.

In addition, in the case of a multi-electrode configuration, similarly to the situation with a purely bipolar arrangement, it is possible to entirely omit the neutral electrode or electrodes. In that way the flow of current remains limited to the target region, and secondary effects as are known from the monopolar mode of application can therefore no longer occur.

The measuring unit is preferably adapted to derive from a measured impedance the omit resistance between a predetermined number of active electrodes (5, 6) of a sub-array (19) of all connected electrodes. That is preferably effected by determining the ohmic or active resistance R for low values of R (0-200 ohms) insofar as the quotient is formed from a measured active power and the square of a measured current. For high values of R (from about 4200 ohms) R in contrast is crucially determined by the quotient between the square of a measured voltage and a power which is measured at the same time. The advantage of this alternative configuration is that control of the power for tissue ablation can be effected in crucially dependent relationship on the ohmic tissue resistance which is actually of interest while control in dependence on the measured impedance is adversely affected to a greater degree by a variable reactive impedance component, for example by virtue of line capacitances and inductances. The aim of determining the effective ohmic resistance is to reduce the influence of reactive impedance on actuation of the electrodes using simple means.

The application apparatus according to the invention for applying a high frequency current for thermal sclerosis of body tissue, includes an electrode array with at least three active electrodes which can be introduced into body tissue, a high frequency generator for producing a high frequency voltage, which generator is to be switchably connected to one or more of the electrodes, and a measuring device for measuring the impedance or the ohmic resistance of the tissue between all or selected active electrodes. The application apparatus further includes a selector device which is connected to the measuring device and adapted to select a sub-array including at least two active electrodes from the electrode array on the basis of the measured impedance or the ohmic resistance. There is also a control device which is connected to the selector device and which is adapted to apply the high frequency voltage to the active electrodes of the selected sub-array in such a way that a high frequency current flows between them through the body tissue.

In this case the term sub-array is used to denote any portion of the electrode array, which includes at least two active electrodes, including the situation where the entire electrode array is selected as the sub-array. As the impedance and in particular ohmic resistance as volume information about the tissue properties represents a measurement in respect of advance of the sclerosing effect, impedance or active resistance measurement is suitable for establishing differing degrees of sclerosing in the region of the tissue to be sclerosed. The various tissue regions can then be treated in a specifically targeted fashion by the application of the high frequency voltage to selected active electrodes of the electrode array. In that respect the selection of the electrodes, that is to say the formation of the sub-array, determines the current paths through the tissue to be sclerosed.

In an embodiment of the invention the selector device is of such a configuration that a new impedance or active resistance measurement operation and a new selection of a sub-array including at least two active electrodes is effected when a predetermined time has elapsed since the preceding selection.

Applying the high frequency current only over a predetermined time and the new selection of the sub-array on the basis of a new impedance or active resistance measurement means that the advance of the sclerosing process can be checked at predetermined intervals and further application can be adapted to the advance detected. In that respect the new selection affords the possibility of selecting a different sub-array of electrodes from the sub-array which had been previously used, and in that way to react to progressive sclerosing with altered current paths in the tissue to be sclerosed. That is advantageous in particular when sclerosing is not effected uniformly in all of the tissue to be sclerosed but advances locally at differing speeds. In addition, burning of the treated tissue regions due to excessively long application of the high frequency current can be avoided by chronologically limiting the period of application.

In a further configuration of the invention the measuring device is adapted to measure the impedance or active resistance of the body tissue during the application of the high frequency current. The measured impedances or active resistance values can be related for example to reference values which have been measured before the beginning of the electrothermal treatment. That configuration affords the advantage that the progress of sclerosing is continuously detected on the basis of impedance or active resistance measurement at the tissue between the electrodes, in particular on the basis of the change in the impedance or active resistance values in relation to the reference values. The duration of application of the high frequency current by way of the electrode sub-array can thus be determined in dependence on the progress of sclerosing. Comparison of the measured impedance or active resistance values to the previously ascertained reference values makes it possible to take account, when determining the application duration, of unwanted influences on the measured impedance or active resistance values which result for example from different spacings between the various electrodes or from differing impedances, which already prevailed prior to the commencement of treatment, in respect of various tissue regions to be treated.

Advantageously the selector device is so designed that a new selection of a sub-array including at least two active electrodes is effected if the impedance or the active resistance of the body tissue between a predetermined number of active electrodes of the sub-array reaches or exceeds a predetermined value.

The fact that a predetermined impedance or active resistance value is reached or exceeded indicates that sclerosing has progressed to a given degree. The sclerosing procedure can then be progressed at another part, which has not yet sclerosed to such an extent, of the tissue which is to be sclerosed. That makes it possible to avoid unnecessarily long application durations and patient stresses resulting therefrom. In addition it is also possible to particularly effectively avoid burning the tissue due to excessively long application of the high frequency current at a tissue region.

Time-dependent and impedance-dependent selection can also be combined so that a new selection takes place whenever a predetermined time has elapsed or a predetermined impedance or a predetermined active resistance is reached.

In still a further configuration of the invention the selector device is of such a configuration that prior to the selection or the fresh selection of the sub-array including at least two active electrodes it causes the measuring device to implement a measurement in respect of the impedance or the active resistance of the body tissue between all possible pairs of active electrodes and selects as the sub-array those active electrodes between which the impedance or the active resistance is at its smallest or does not exceed a predetermined value.

By virtue of the fact that, in the fresh selection, those active electrodes between which the body tissue exhibits the lowest impedance or the lowest active resistance are selected, the high frequency voltage can be targetedly applied to those regions of the tissue in which sclerosing is advanced to the lowest degree.

An advantageous development of the application apparatus according to the invention is distinguished in that the control device is of such a configuration that at the beginning of the application procedure the high frequency voltage is applied to the active electrodes in a predetermined cyclic change and the selection of the sub-array including at least two active electrodes on the basis of impedance or ohmic resistance occurs at a later moment in time in the application procedure. At the beginning of the application operation the impedance or the active resistance in the whole of the tissue to be sclerosed frequently is still at an identical or approximately identical value. The local differences in the impedance or active resistance only occur in the course of the application procedure so that a selection of the electrodes, which is adapted to the impedance or active resistance, becomes meaningful only in the course of the application procedure.

In a further advantageous development the application apparatus is distinguished in that the selector device is designed in such a way that at least three active electrodes are selected as the sub-array and the control device is designed in such a way that the active electrodes are acted upon by high frequency voltages which are respectively phase-shifted with respect to each other by a fixed phase angle. The phase-shifted high frequency current results in improved homogeneity of the applied high frequency current in the tissue to be sclerosed.

Advantageously three active electrodes are selected as the sub-array, the phase angles being 120 degrees. That makes it possible to operate the active electrodes with three-phase current.

The selector device or the control device is preferably so designed that it switches off sub-arrays or electrode combinations for which the impedance or ohmic resistance exceeds a predetermined maximum value $R_{max}$. Tissue sclerosing is then terminated in the corresponding volume element.

Additionally or alternatively the control device is adapted to reduce to a predetermined measure a maximum power $P_{max}$ which is to be delivered and which is predetermined by way of a respectively selected sub-array when a defined impedance or a defined ohmic resistance smaller than $R_{max}$ is exceeded. In that way, shortly before sclerosing is concluded, this prevents the selected sub-array of electrodes being prematurely switched off by virtue of pure drying-out of the substantially sclerosed tissue.

Preferably the selector device or the control device is designed in such a way that it switches off sub-arrays or electrode combinations for which the impedance or ohmic resistance falls below a predetermined minimum value $R_{min}$. It is possible in that way to detect short-circuits and to prevent the patient from being endangered.

Preferably the control device initially adjusts lower a power delivered by way of a respectively selected sub-array after the selection of the sub-array and increases the power within a predetermined time in one or more stages or continuously to a predetermined maximum power $P_{max}$. That avoids an effect referred to as the 'popcorn effect' which is due to the fact that, when maximum power is abruptly applied, possible vapor bubbles cannot be sufficiently quickly dissipated so that the tissue is ruptured or lifted off the electrode needle by the pressure which suddenly occurs.

In an advantageous configuration of the invention the active or selected electrodes of the application apparatus are arranged on electrode needles which permit accurate arrangement of the active electrodes in the tissue region to be sclerosed or around the tissue region to be sclerosed.

The electrode needles can be in the form of bipolar electrode needles, that is to say they may each include two mutually insulated active electrodes which can be acted upon independently of each other by high frequency voltage. In that way it is possible for the high frequency current to be caused to flow not only between different electrode needles but also along an individual electrode needle, which increases the variability in the current paths and thus the number of individually sclerosable portions of the tissue region to be sclerosed.

The variability factors can be further enhanced by the use of multipolar electrode needles, that is to say electrode needles having more than two active electrodes.

An advantageous development of the electrode needles is distinguished in that they are surrounded by an insulating enclosure from which they can be extended by predetermined lengths so that the number of electrodes of the multipolar electrode needles can be adjusted by extending the electrode needles from the enclosure and retraction thereof.

An electrode needle can have one or more passages for a fluid for cooling or heating the active electrodes or the entire needle. In particular gases or liquids are considered as the fluid. Heating or cooling can be used for homogenising the rise in temperature of the tissue which occurs due to the high frequency current, that is to say the temperature pattern in the tissue. The passages for the fluid can also be used in the hitherto usual electrode needles for achieving a more homogeneous temperature pattern.

In a configuration the passages are distinguished in that they lead to the active electrodes and are suitable for feeding cooling fluid. The rise in temperature of the tissue is at the greatest where the current density of the high frequency current is at its highest. Typically the current density is highest at the active electrodes. Cooling the electrodes can reduce the temperature of the tissue directly adjoining the electrodes and thus result in a more homogeneous pattern in respect of temperature in the tissue.

In an embodiment the fluid is a deionised liquid. Liquids typically have a higher thermal coefficient than gases but are generally electrically conductive so that it is necessary to provide for good electrical insulation of the passages. The use of deionised and therefore non-conducting liquids means that it is possible to substantially forego the electrical insulation for the passages. The better the degree of deionisation of the liquid, the correspondingly less extensive and expensive the insulation needs to be.

BRIEF DESCRIPTION OF THE DRAWINGS

Further features and advantages of the present invention are described hereinafter by means of a detailed embodiment by way of example with reference to the accompanying drawings in which.

DETAILED DESCRIPTION OF PREFERRED EMBODIMENT(S)

Figure 1:
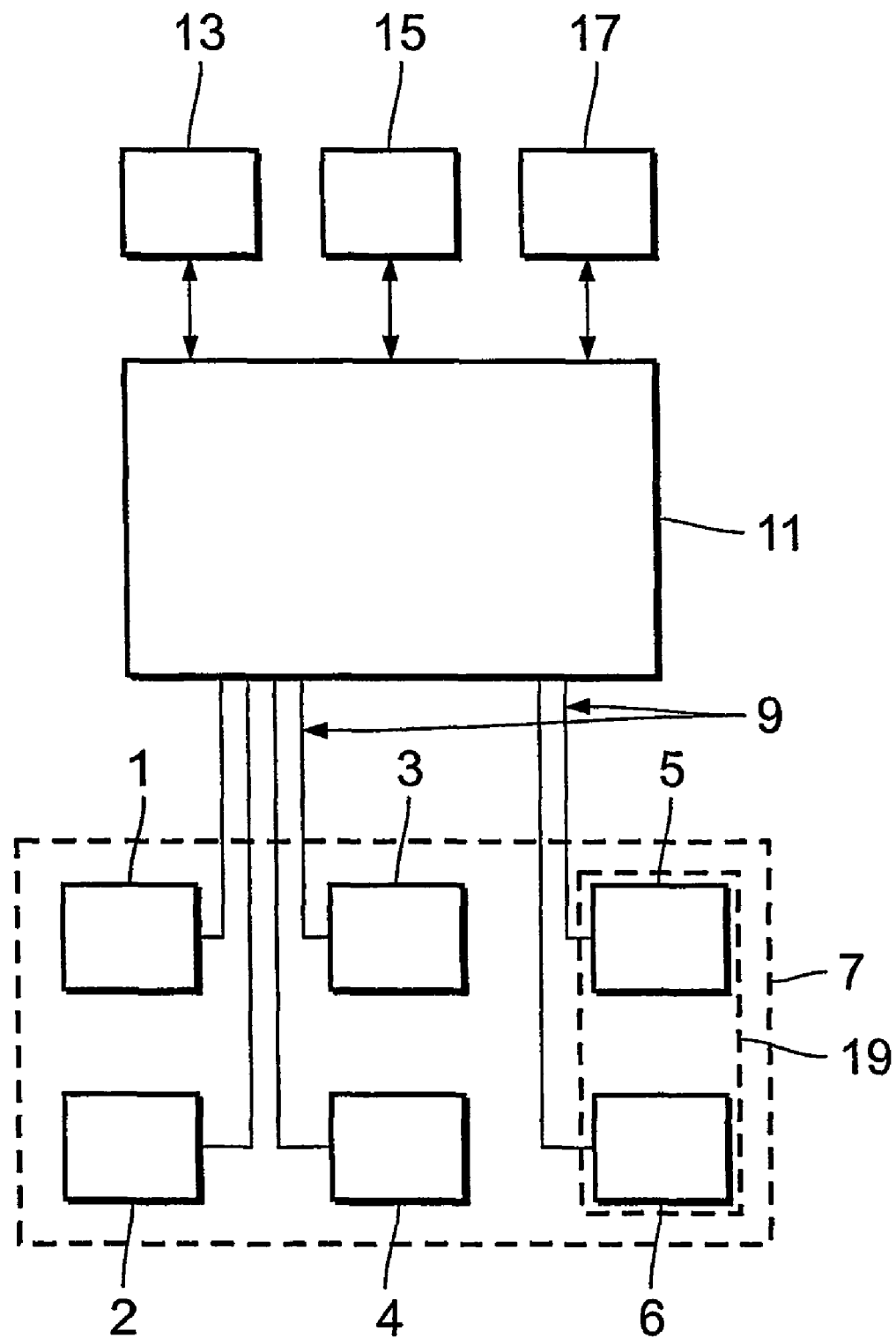
FIG. 1 is a block circuit diagram showing the components of the present invention.

FIG. 1 is a block circuit diagram of an embodiment by way of example of the apparatus according to the invention for sclerosing body tissues. The apparatus includes a number of active electrodes 1 through 6 which together form an electrode array 7. The electrodes 1 through 6 are each connected to a control unit 11 by way of respective individual lines 9. Also connected to the control unit 11 are a measuring device 13 for measuring the impedance or active resistance of the tissue between the electrodes 1 through 6, a selector device 15 for selecting electrodes and a high frequency generator 17 for producing high-frequency ac voltages.

In a multipolar use the high frequency generator 17 has for example an output power of 250 W at 20-50Ω, at a working frequency of 470 kHz. In the case of bipolar uses the output power is for example 125 W at 100Ω, also at a working frequency of 470 kHz. The working range of the high frequency generator is between 10 and 1000Ω. Impedance or active resistance measurement by the measuring device 13 can be effected either at the working frequency of 470 kHz or however at another frequency, in particular a lower frequency, for example 20 kHz. The high frequency generator is designed in such a way that it is suitable for typical application times of 20 minutes and longer at full load.

The measuring device 13 is designed in such a way that it is capable of measuring the impedance or active resistance of the tissue between each two respective electrodes of the electrode array 7. The measuring operation can be effected for example by a procedure whereby an ac voltage is applied between two electrodes of the electrode array 7 and the measuring device 13 then measures the alternating current flowing through the two electrodes. In that respect it is sufficient to measure the magnitude of the impedance, that is to say the active resistance of the tissue. Alternatively however the measuring device 13 can also ascertain the phase angle between the alternating current flowing through the two electrodes and the ac voltage applied to the electrodes so that it is possible for the impedance to be completely determined. From the result of impedance measurement the selector device 15 can determine the degree of sclerosing of the tissue between the two electrodes. The higher the degree of sclerosing, the correspondingly higher is the impedance of the tissue.

In order to be able to take account of the frequency dependency of the impedance when determining the condition of the tissue, impedance measurement can be effected at a plurality of frequencies. The information contained in the frequency dependency of impedance can be taken into consideration for example when determining application parameters for application of the high frequency current.

The described impedance measuring operation is effected in the present embodiment for all possible pairs of electrodes of the electrode array 7 so that the selector device 15 can afford impedance values for all tissue regions between each two respective electrode pairs. Then, on the basis of those impedance values, the selector device 15 selects at least two electrodes of the electrode array 7, which form a sub-array of the electrode array 7.

The selector device 15 communicates the selected sub-array to the control unit 11 which then, by way of the lines 9, feeds the high frequency voltage generated by the high frequency generator 17 to the electrodes of the sub-array 19, here the electrodes 5 and 6. For that purpose the control unit 11 includes a switching unit, by means of which the lines 9 can be individually connected to the high frequency generator 17. The high frequency generator 17 can be for example a constant current or a constant voltage source.

When the high frequency voltage is applied to the electrodes 5 and 6 of the sub-array 19, a high frequency alternating current flows between them, which results in a rise in temperature of the tissue and as a consequence thereof denaturing of the tissue. After a predetermined period of time the control unit 11 terminates the feed of the high frequency voltage to the electrodes of the sub-arrays 19 and causes the measuring device 13 to again measure the impedance between all possible electrode pairs of the electrode array 7. The selector device 15 then selects for example from the electrode array the pair of electrodes between which the tissue has the slightest impedance rise, as the sub-array 19. The impedance values can possibly also be weighted differently with weighting factors. The selected electrode pair can be the same electrode pair 5, 6 as in the preceding selection process or a different electrode pair. The latter will be the case if, by virtue of the electrothermal treatment, the impedance of the tissue between the electrodes 5 and 6 has risen in such a way that it is higher than the impedance of the tissue between at least one other pair of electrodes.

A sub-array 19 of the electrode array 7 can also include more than two electrodes. In that case it may be appropriate to predetermine an impedance threshold which presets whether a high frequency current is or is not to be fed to the tissue between the corresponding pairs of electrodes. If the impedance of the tissue between a pair of electrodes does not reach or exceed the impedance threshold the pair of electrodes in question is incorporated into the sub-array 19.

In an alternative configuration of the invention, during application of the high frequency current, the measuring device 13 continuously measures the impedance between the electrodes and outputs a signal to the control device 11 as soon as the impedance or the rise in impedance of the tissue between the electrodes 5 and 6 exceeds a predetermined threshold value. The control device then terminates application of the high frequency current. After application of the high frequency current is terminated the control device 11 causes the measuring device 13 to again measure the impedance of the tissue between all pairs of electrodes and thereafter, on the basis of the result of the impedance measurement procedure, causes the selector device 15 to select a fresh sub-array 19 of the electrode array 7, by way of which the high frequency current is then fed to the tissue.

If the sub-array 19 includes more than two electrodes, it can be provided that the control device 11 terminates application of the high frequency current as soon as the impedance between one of the electrode pairs exceeds a predetermined value or alternatively when, with a predetermined number of electrode pairs, the tissue disposed therebetween exceeds the predetermined impedance threshold.

Figure 2:
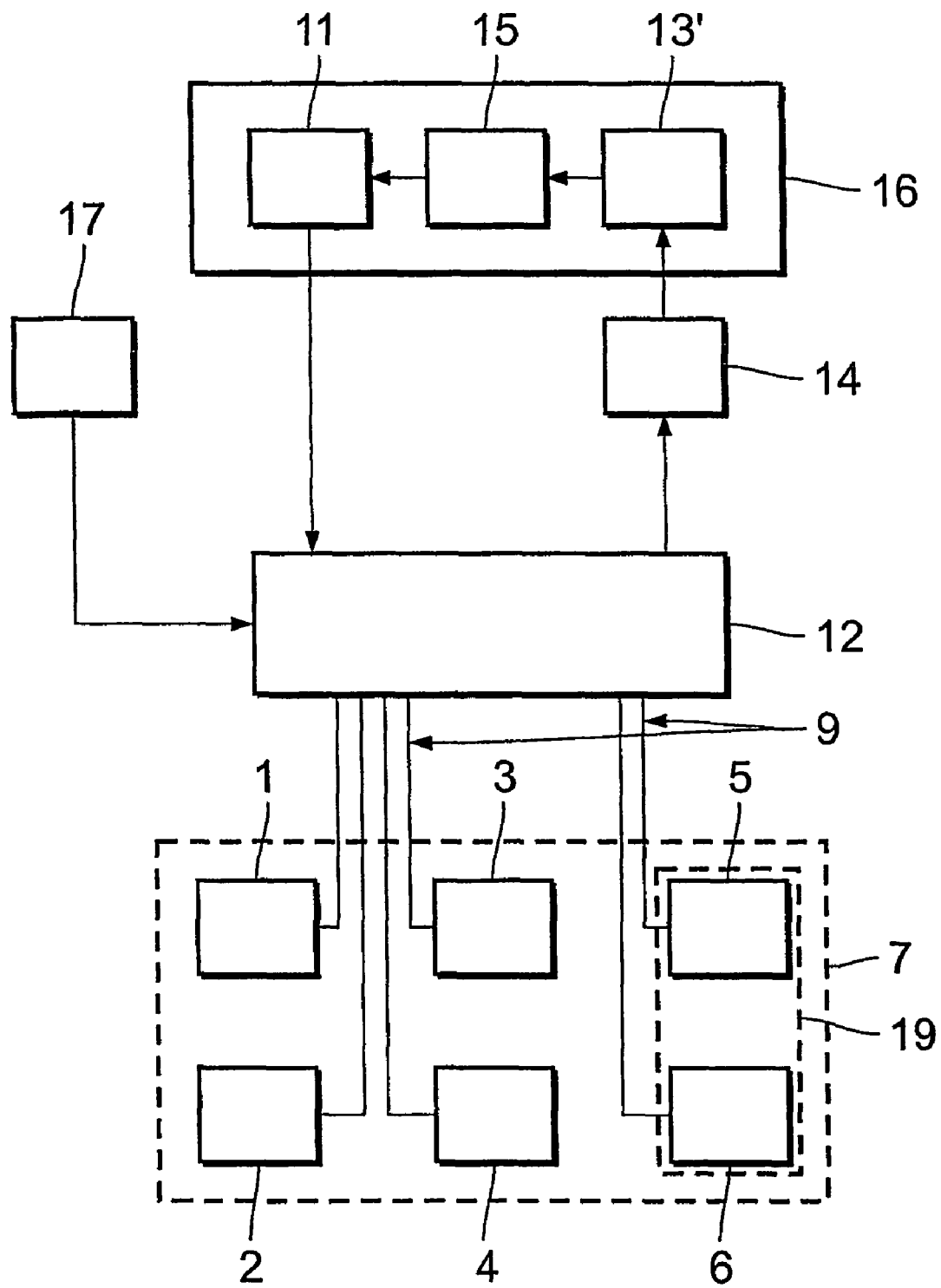
FIG. 2 is a block circuit diagram showing an alternative configuration of the invention.

An alternative configuration of the invention is shown as a block circuit diagram in FIG. 2. The same components as in the embodiment illustrated in FIG. 1 are denoted by the same references and are not further described hereinafter.

This alternative configuration differs from that shown in FIG. 1 in that there is a switching unit 12 in the form of a unit which is separate from the control unit 11. Directly connected to the switching unit 12 is the high frequency generator 17 and an A/D converter 14 for converting the analog signals resulting from impedance measurement into digital signals which are delivered to a processor 16. The switching unit 12 is adapted to connect each electrode 1-6 individually to the high-frequency generator 17 and/or the A/D converter 14.

The processor 16 includes the measuring or evaluation unit 13' which is connected to the A/D converter 14 for receiving the digital signals resulting from impedance measurement, and ascertains the impedance of the body tissue from the received signals. The evaluation unit 13' is also connected to the selector unit 15, for the output of the impedance values, the selector unit 15 in turn being connected to the control unit 11. The selector unit 15 selects the active electrodes to be used (in the illustrated embodiment the electrodes 5 and 6) on the basis of the impedance values and then notifies the selection to the control unit 11. In accordance with that selection the control unit 11 acts on the switching unit 12 by way of a control line so that it connects the selected active electrodes to the high frequency generator 17.

Alternatively the control unit 11 can additionally be connected to the high frequency generator 17 by way of a control line in order to be able to adjust the frequency of the high frequency voltage delivered by the high frequency generator 17.

Figure 3A:
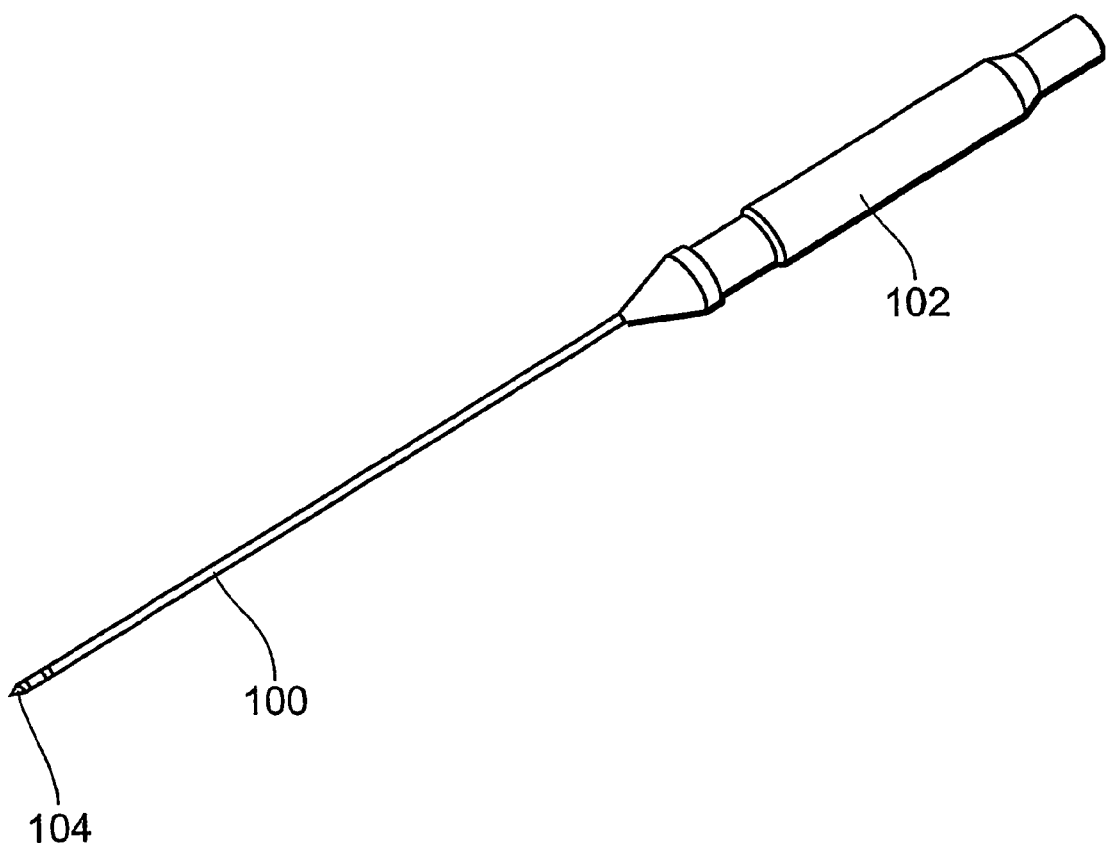
FIGS. 3a and 3b show an electrode needle for use in the apparatus according to the invention.
Figure 3B:
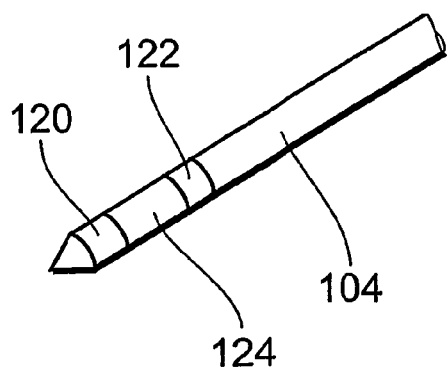

In the illustrated embodiments the active electrodes are in the form of electrode needles. Such an electrode needle is shown in FIG. 3a. At its proximal end, that is to say the end which projects out of the tissue, the electrode needle 100 has a gripping region 102 while at its distal end, that is to say the end 104 which is intended to be introduced into the tissue, it has two active electrodes 120 and 122 (see FIG. 3b). Disposed between the two electrodes 120 and 122 is an insulating region 124 which electrically insulates the two electrodes from each other. Although the electrode needle shown in FIGS. 3a and 3b has two electrodes, the electrode needle may also have more than two active electrodes or only one electrode. If there are more than two electrodes there is a respective insulating region between all electrodes. All electrodes of an electrode needle 100 are connected to a control device (not shown) by way of respective individual lines in such a way that a high frequency voltage can be individually fed to each electrode.

In its interior the electrode needle 100 may also include one or more passages for feeding a fluid in order to cool or heat the active electrodes or the entire needle.

Figure 4A:
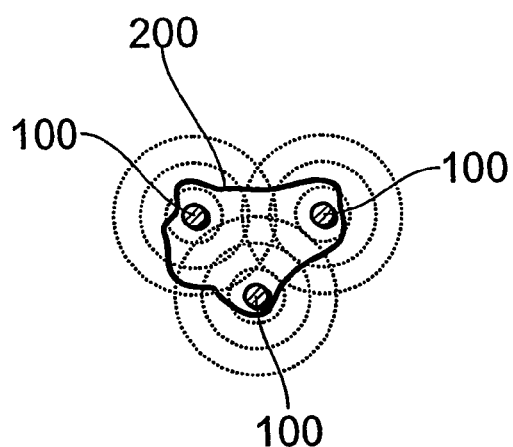
FIGS. 4a and 4b show an arrangement by way of example of the electrode needles in the tissue as a plan view and a side view and the associated current flows.
Figure 4B:
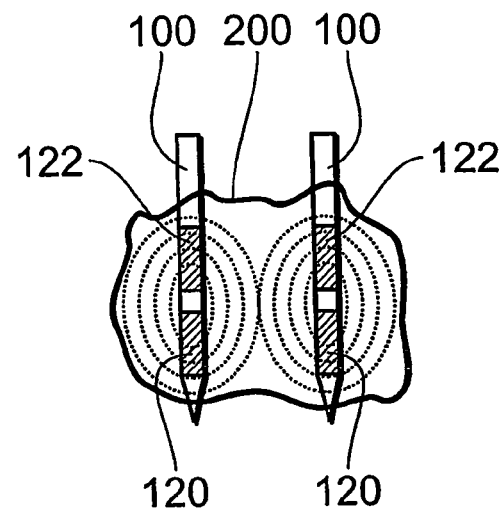

FIGS. 4a and 4b diagrammatically show a first example of the use of the application apparatus. The Figures show a pathological tissue 200, the target tissue, into which three electrode needles 100 are introduced by puncturing in such a way that their active electrodes 120 and 122 are in direct electrical contact with the target tissue.

The electrodes 120 and 122 are firstly acted upon with a high frequency voltage by the control unit 11 in such a way that a high frequency current flows along the electrode needles 100 in the axial direction between the electrodes 120 and 122. Those current flows are indicated in FIG. 4b and the corresponding potentials in FIG. 4a by broken lines.

FIG. 4a shows a plan view of the three electrode needles 100 while FIG. 4b shows a side view of two of the three electrode needles 100. By virtue of the superimposition of the current flows of all three electrode needles 100, a tissue region involving a homogeneous current flow is produced between the needles so that it is possible to achieve homogeneous heating of the tissue region.

Simultaneously with the application of the high frequency current, the tissue impedance between the electrodes 120 and 122 is measured, at the working frequency or however another frequency, by the measuring device 13. Particularly if a frequency which does not correspond to the working frequency is adopted for that purpose, then with ongoing application the impedance of the tissue can be measured between individual pairs of electrodes without the application current substantially impeding that measurement procedure. For that purpose the measuring device includes a frequency discriminator or filter which is capable of separating the frequency of impedance measurement, for example 20 kHz, from the working frequency, for example 470 kHz.

Figure 5A:
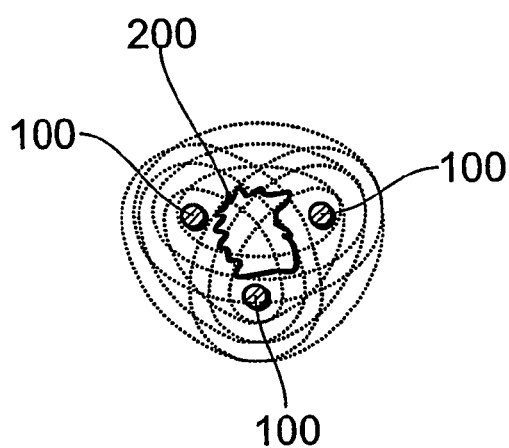
FIGS. 5a and 5b show a further arrangement by way of example of the electrode needles in the tissue as a plan view and a side view and the associated current flows.
Figure 5B:
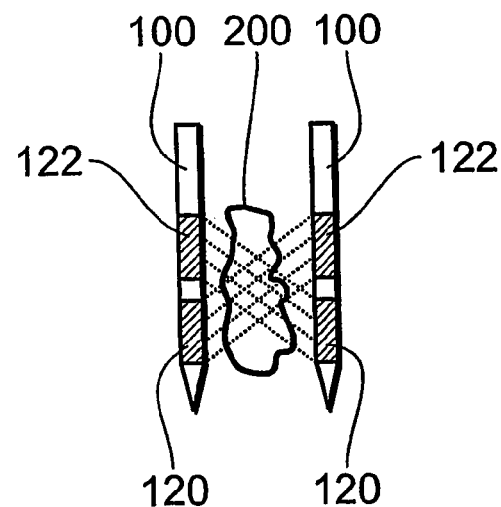

FIGS. 5a and 5b show a further example of the use of the application apparatus according to the invention. Instead of being introduced into the target tissue, in this embodiment three electrode needles 100 are inserted by puncturing just outside the target tissue so that the target tissue is disposed between the three electrode needles 100. In contrast to the example shown in FIGS. 4a and 4b, in this case the current flow is not in parallel relationship with the axes of the needles, but from one electrode needle 100 to the other. It is possible in that way to achieve a homogeneous current flow in the target tissue 200. In addition it is possible to avoid the entrainment of malignant tissue upon removal of the electrode needles.

The application apparatus can be operated either exclusively with an axial current flow along the needles, exclusively with a current flow between two different needles or with a combination of both. The direction of the current flow can be switched over from one mode to the other after a fresh selection of the sub-array of active electrodes.

Although electrode arrays with six electrodes are shown in each of the embodiments by way of example, the electrode array may also include more or fewer than six electrodes.

The invention claimed is:

1. An application apparatus for applying a high frequency current for thermal sclerosis of body tissue, including a connected electrode array with at least three active electrodes which can be introduced into body tissue, a high frequency generator for producing a high frequency voltage, which generator is to be switchably connected to one or more of the electrodes, and a measuring device for measuring the impedance of the body tissue between all or selected active electrodes, characterised by a selector device which is connected to the measuring device and which is adapted to select a sub-array including at least two active electrodes from the electrode array on the basis of the measured impedance, and by a control device which is connected to the selector device and which is adapted to apply the high frequency voltage to the active electrodes of the selected sub-array in such a way that a high frequency current flows between them through the body tissue, characterized in that the selector device is of such a configuration that prior to the selection or the fresh selection of the sub-array including at least two active electrodes it causes the measuring device to implement a measurement in respect of the impedance or the ohmic resistance of the body tissue between all possible pairs of active electrodes and selects as the sub-array those active electrodes between which the impedance, the ohmic resistance, the change in impedance or the change in ohmic resistance is at its smallest.

2. An application apparatus as set forth in claim 1 characterized in that the selector device is of such a configuration that it automatically performs a new impedance measurement operation and a new selection of a sub-array including at least two active electrodes when a predetermined time has elapsed since the preceding selection.

3. An application apparatus as set forth in claim 1 characterized in that the selector device is designed in such a way that it automatically effects a fresh selection of a sub-array including at least two active electrodes if the impedance, the ohmic resistance, the change in impedance or the change in the ohmic resistance of the body tissue between a predetermined number of active electrodes of the sub-array reaches or exceeds a predetermined value.

4. An application apparatus as set forth in claim 1 characterized in that the control device is of such a configuration that at the beginning of the application procedure the high frequency voltage is applied to the active electrodes in a predetermined cyclic change and the selection of the sub-array including at least two active electrodes on the basis of impedance or ohmic resistance occurs at a later moment in time in the application procedure.

5. An application apparatus as set forth in claim 1 characterized in that the selector device or the control device is so designed that it switches off sub-arrays or electrode combinations for which the impedance or ohmic resistance exceeds a predetermined maximum value $R_{max}$, and does not take account thereof again in the further procedure.

6. An application apparatus as set forth in claim 5 characterized in that the control device is adapted to reduce to a predetermined measure a maximum power $P_{max}$ which is to be delivered and which is predetermined by way of a respectively selected sub-array when a defined impedance or a defined ohmic resistance smaller than $R_{max}$ is exceeded.

7. An application apparatus as set forth in claim 1 characterized in that the selector device or the control device is designed in such a way that it switches off sub-arrays or electrode combinations for which the impedance or ohmic resistance falls below a predetermined minimum value $R_{min}$.

8. An application apparatus as set forth in claim 1 characterized in that the control device initially adjusts lower a power delivered by way of a respectively selected sub-array (19) after the selection of the sub-array and increases it within a predetermined time in one or more stages or continuously to a predetermined maximum power $P_{max}$.

9. An application apparatus as set forth in claim 6 characterized in that the selector device is designed in such a way that as a sub-array it selects at least three active electrodes and the control device is designed in such a way that the active electrodes are acted upon with high frequency voltages which are respectively phase-shifted relative to each other by a fixed phase angle.

10. An application apparatus as set forth in claim 9 characterized in that the selected sub-array includes three active electrodes and the phase angles are 120 degrees.

11. An application apparatus as set forth in claim 1 characterized in that the active electrodes are arranged on electrode needles.

12. An application apparatus as set forth in claim 11 characterized in that the electrode needles are bipolar electrode needles.

13. An application apparatus as set forth in claim 12 characterized in that the electrode needles are multipolar electrode needles.

14. An application apparatus as set forth in claim 11 characterized in that the electrode needles are surrounded by an insulating enclosure and can be extended from the enclosure by predetermined lengths.

15. An application apparatus as set forth in claim 11 characterized in that the electrode needles have passages for a fluid for cooling or heating the electrode needles.

16. An application apparatus as set forth in claim 15 characterized in that the passages lead to the active electrodes and are suitable for feeding cooling fluid.

17. An application apparatus as set forth in claim 15 characterized in that the fluid is a deionized liquid.

18. An application apparatus as set forth in claim 1 characterized in that the high frequency generator, the measuring device, the selector device and the control device are combined together in one or more housings to form an application generator which has plug connections for the electrodes and the feed lines thereof.

19. An application apparatus for applying a high frequency current for thermal sclerosis of body tissue according to claim 1, including a connected electrode array with at least three elongate electrode needles, each said needle having two active electrodes, electrically insulated from one another, which can be introduced into body tissue.

20. An application apparatus for applying a high frequency current for thermal sclerosis of body tissue according to claim 19, wherein said two active electrodes on each said needle are spaced longitudinally along the needle, with an insulated region longitudinally therebetween.

21. An application apparatus for applying a high frequency current for thermal sclerosis of body tissue according to claim 20 wherein each said electrode needle further includes an electrically non-conductive gripping portion spaced longitudinally from said active electrodes.

22. A method for thermally schlerosing body tissue, comprising the steps of:
   a) providing an electrode array with at least three active electrodes, each said electrode being in the form of an electrode needles each bearing two electrically-conductive electrodes insulated from one another;
   b) providing a high frequency generator, for producing a high frequency voltage, said generator being switchably connected to one or more of the electrodes;
   c) providing a measuring device electrically coupled to at least one of said electrodes, for measuring the impedance of body tissue between all or selected active electrodes,
   d) providing a selector device which is connected to the measuring device and which is adapted to select a sub-array including at least two active electrodes from the electrode array on the basis of the measured impedance;

e) providing a control device which is connected to the selector device and which is adapted to apply the high frequency voltage to the active electrodes of the selected sub-array in such a way that a high frequency current flows between them through the body tissue;

f) positioning the electrode array adjacent tissue to be schlerosed;

g) applying current to the electrode array at a first frequency, generating heat between active electrodes sufficient to schlerose the tissue;

h) while applying current, measuring the impedance between two active electrode needles;

i) prior to application of current, measuring impedence between every pair of electrode needles within said array and identifying the pair of electrode needles having the lowest impedence therebetween;

j) applying current to the pair of electrode needles having the lowest impedence therebetween.

23. A method for thermally schlerosing tissue according to claim 22, further comprising the step of:

i) ceasing application of current when the measured impedance reaches a threshold.

* * * * *